United States Patent
Anderson

(10) Patent No.: US 7,789,091 B2
(45) Date of Patent: Sep. 7, 2010

(54) METHOD AND APPARATUS FOR REMOVING DRY SKIN

(76) Inventor: Christy Anderson, 412 E. Yearling Rd., Phoenix, AZ (US) 85085

( * ) Notice: Subject to any disclaimer, the term of this patent is extended or adjusted under 35 U.S.C. 154(b) by 778 days.

(21) Appl. No.: 11/543,409

(22) Filed: Oct. 5, 2006

(65) Prior Publication Data

US 2008/0086151 A1  Apr. 10, 2008

(51) Int. Cl.
A45D 29/18  (2006.01)
(52) U.S. Cl. .................................... 132/76.4
(58) Field of Classification Search ............... 132/76.4, 132/200; 606/131
See application file for complete search history.

(56) References Cited

U.S. PATENT DOCUMENTS

| | | | | |
|---|---|---|---|---|
| 3,169,264 A | * | 2/1965 | Walker | ............... 15/118 |
| 5,275,181 A | * | 1/1994 | Rudolph, Jr. | ............... 132/76.4 |
| 5,412,830 A | * | 5/1995 | Girardot et al. | ............... 15/118 |
| 6,510,577 B1 | * | 1/2003 | Borcherds et al. | ............... 15/118 |
| 6,656,565 B2 | * | 12/2003 | Harrison | ............... 428/131 |
| 2002/0153019 A1 | * | 10/2002 | Ayzman | ............... 132/76.5 |
| 2006/0191553 A1 | * | 8/2006 | Anderson et al. | ............... 132/76.4 |
| 2008/0091216 A1 | * | 4/2008 | Grace et al. | ............... 606/131 |

* cited by examiner

Primary Examiner—Robyn Doan
Assistant Examiner—Brianne O'Neill
(74) Attorney, Agent, or Firm—Holme Roberts & Owen LLP

(57) ABSTRACT

The invention generally describes a method an apparatus for removing dry or dead skin from an area to be exfoliated. More particularly, the invention provides a skin removal device having a flexible screen member and a first border member attached to the perimeter of the screen member and a method for using the same. The flexible screen member's surface has an abrasive coating and plurality of holes throughout the device used to exfoliate and remove dry or dead skin from the targeted area. The flexible screen member is placed over the targeted area and moved so that the dry or dead skin is removed from the area and passed through the flexible screen member to the surface not contacting the area.

13 Claims, 3 Drawing Sheets

METHOD AND APPARATUS FOR REMOVING DRY SKIN

BACKGROUND OF THE INVENTION

1. Field of the Invention

The invention pertains generally to a health and beauty product and more particularly to a method and apparatus for removing dry or dead skin.

2. The Relevant Technology

Many people suffer from dry skin, particularly on the heels of their feet. Such a condition is often more pronounced in dry climates with low humidity levels. In extreme instances, a person's skin, and particularly the heels, can even become cracked while producing numerous additional layers of hardened skin.

There are numerous health and beauty products available that aid in removing or exfoliating dead skin from areas of the body. For example, pumice stones and other abrasive devices are available to exfoliate, smooth and eliminate dry or dead skin. Such devices sand the area to be exfoliated in a back and forth or circular motion to remove the dry or dead skin cells. However, such products do not exfoliate a substantial quantity of dry or dead skin while simultaneously sanding the area. When such devices are used, the exfoliated skin cells accumulate between the area and the abrasive surface, which greatly reduces the friction between the two surfaces. The exfoliated waste is also trapped in pits within the cracks of one's heels as well as pits within the exfoliating device itself. Such conditions result in a degradation in the exfoliating device's effectiveness.

It is therefore desirable to provide a health and beauty device that removes dry or dead skin cells from the body as well as the abrasive surface contacting the skin in conjunction with the exfoliation process. Under typical conditions and operations, the skin care professional who seeks to exfoliate a significant number of layers of dead or dry skin cells, such as those processes typical to pedicure treatments, will utilize a razor device to cut through a number of layers of skin to reach the desired effect. It is therefore further desirable to provide an exfoliation device that is less invasive and less painful to the subject, but also provides an equivalent effectiveness and result, than that which occurs from using a razor type device to exfoliate or remove a number of dry or dead skin cells from the body.

BRIEF SUMMARY OF THE INVENTION

The invention pertains generally to an apparatus for removing dry skin from the body. The apparatus generally comprises a flexible, porous screen member having a plurality of holes. The screen's surface has an abrasive coating to permit removal of dry skin from a targeted area for exfoliating. The apparatus also includes a border affixed to an edge of the screen. The plurality of holes in the screen allow dry skin to pass through the flexible screen member from the first surface that contacts the targeted area for exfoliating to the second surface of the screen member. The abrasive coating typically comprises silicon carbide.

The invention also pertains to a method for exfoliating dry or dead skin from an area of the human body. The method comprises providing a skin removal device having a flexible screen member and a first border. The flexible screen member further comprises a plurality of holes and a surface having an abrasive coating to allow removal of dry skin from an area to be exfoliated. The method further comprises positioning the surface of the skin removal device having the abrasive coating over an area to be exfoliated and contacting the surface with the area. Pressure is applied to the screen member to cause friction between the surface to be exfoliated and the surface of the screen member. The screen member is then moved over the area so that dead or dry skin from the area is removed and passes through the screen member to the surface not contacting the skin.

BRIEF DESCRIPTION OF THE DRAWINGS

The present invention is illustrated by way of example and not limitation in the Figures of the accompanying drawings, in which like references indicate similar elements and in which.

DETAILED DESCRIPTION OF THE PREFERRED EMBODIMENTS

In the following description, numerous specific details are set forth in order to provide an understanding of the present invention. It will be apparent, however, to one skilled in the art that the present invention may be practiced without these specific details. In other instances, well known components or methods have not been described in detail but rather in a block diagram in order to avoid unnecessarily obscuring the present invention. Thus, the specific details set forth are merely exemplary. The specific details may be varied from and still be contemplated to be within the spirit and scope of the present invention.

Reference to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Whereas many alterations and modifications of the present invention will become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as the invention.

Figure 1:
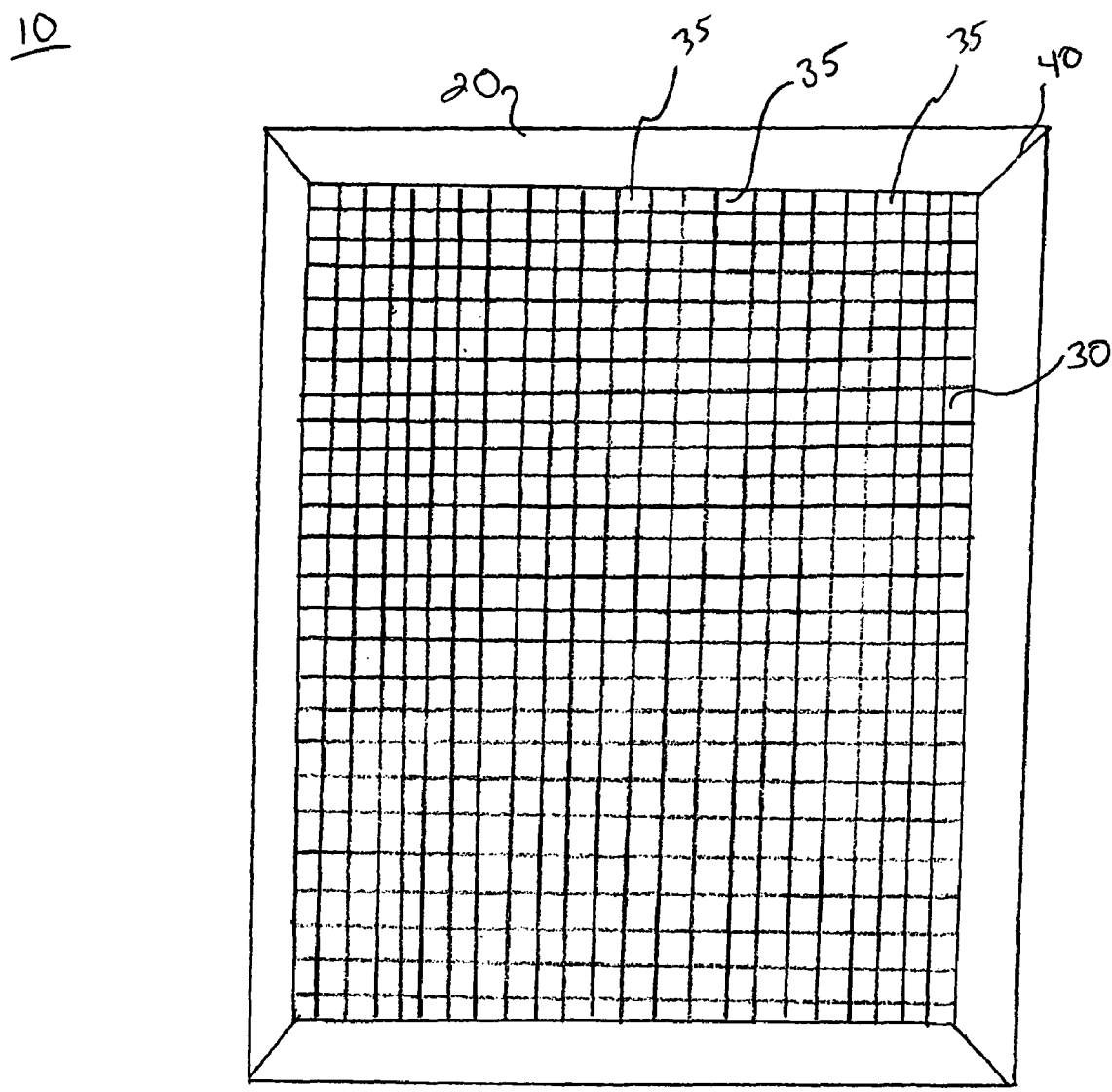
FIG. 1 is a top view of a skin removal apparatus.

FIG. 1 illustrates a top view of a skin removal device 10. Skin removal device 10 generally comprises a flexible, porous screen member 30 and a protective border 20. Flexible screen member 30 has a first surface and a second surface, the first surface shown in the top view of FIG. 1 and the second surface on the reverse side (not shown in FIG. 1). Flexible screen member 30 further has a plurality of holes 32, 33, 35 that pass through the surface of screen member 30. The holes 32, 33, 35 allow dead or dry skin cells to pass through the screen member 30 from the surface contacting the area to be exfoliated, such as the first surface, to the surface not contacting the area, such as the second surface, while sanding the area. The holes also prevent a layer of exfoliated skin cells from forming between the area to be exfoliated and the screen member 30, which would otherwise reduce the effectiveness of the screen member in removing dry or dead skin from the area. Since the present invention allows exfoliated skin to pass through the holes in the screen to be discarded, one may simply tap, blow on or run the screen under water to remove excess waste. During an exfoliating operation, continuous contact is maintained between the skin and the flexible screen member 30. This allows the screen member to exfoliate multiple layers of dry or dead skin cells as each successive layer of skin is removed and passes through the screen member device.

In the illustrated embodiment, skin removal device 10 is 16 square inches, or approximately four-by-four inches in size. A four-by-four device allows the screen to be small enough to fit in the palm of a person's hand, yet large enough to cover a substantial part of the surface area of the location of the body to be exfoliated. Skin removal device 10 is also illustrated in FIG. 1 as generally square in shape. Other sizes and shapes of skin removal device 10 may be used, such as circular or triangular, without deviating from the scope and spirit of the invention.

Under normal conditions, a person's skin comprises a statum coneum, or outermost skin layer, that has approximately 15 to 20 layers of dead skin cells. Typically, this equates to a thickness of 10 to 20 microns. A person with dry and callused feet, for example, can have a statum corneum with a thickness of 100 to 150 microns. Typically, for a pedicure, the pedicurist uses a razor to remove the additional layers of skin. Such an operation, however, is uncomfortable and sometimes painful for the person receiving the skin treatment. In some cases, the razor device can cut too deeply causing injury or bleeding, but most often leaves the feet feeling raw and tender. Device 10 exfoliates the additional 70 to 130 microns of dead skin cells by successively removing each layer, but without the pain associated with use of a razor or similar type product.

Screen member 30 is flexible yet retains its shape. Such flexibility allows the screen to conform to the surface of an area to be exfoliated, such as a person's heel area, as well as fit within the palm of a person's hand. Since it is flexible, the screen member 30 of skin removal device 10 molds to the contour of the area to be exfoliated and therefore maintains a significant amount of surface contact with the area.

Skin removal device 10 has a border 20 that surrounds at least a portion of the edges of screen 30. In one embodiment, the border 20 covers all edges of screen 30. Typically, the edges of screen 30 are sharp, which may cause cuts or abrasions on a person's hands or feet. Therefore, border 20 covers at least a portion of the sharp edges and prevents the edges from having direct contact with the skin. Border 20 may comprise many different materials such as foam, flexible plastic, polyurethane or rubber to name a few. Any other material known by those skilled in the art may be utilized. In the illustrated embodiment, border 20 is manufactured from a foam for its flexibility, low cost and light weight.

Typically, the border is approximately 3/32" thick, one inch wide and runs the length of each side of the screen that it covers. The width of the border is adapted to be folded across the associated edge of the screen so that both the top surface and bottom surface of the screen around the edge is protected. If the total thickness of the border is one inch thick prior to folding on an edge, then the border extends approximately 1/2" inward from the edge of flexible screen member 30 on both the top surface and bottom surface. Border 20 may also act as a gripping surface to hold onto the skin removal device 10. Cut 40 is the dividing point at each corner of screen member 30 between each side of border 20. In the illustrated embodiment, border 20 consists of four individual pieces separated by cut 40. Border 20 may also be a single piece of material that extends along the entire perimeter of screen member 30.

Border 20 is secured to screen member 30 by means of an adhesive such as cyanoacrylate adhesive (i.e., super glue), hot glue or any other adhesive adapted to bond border 20 to screen member 30.

Figure 2:
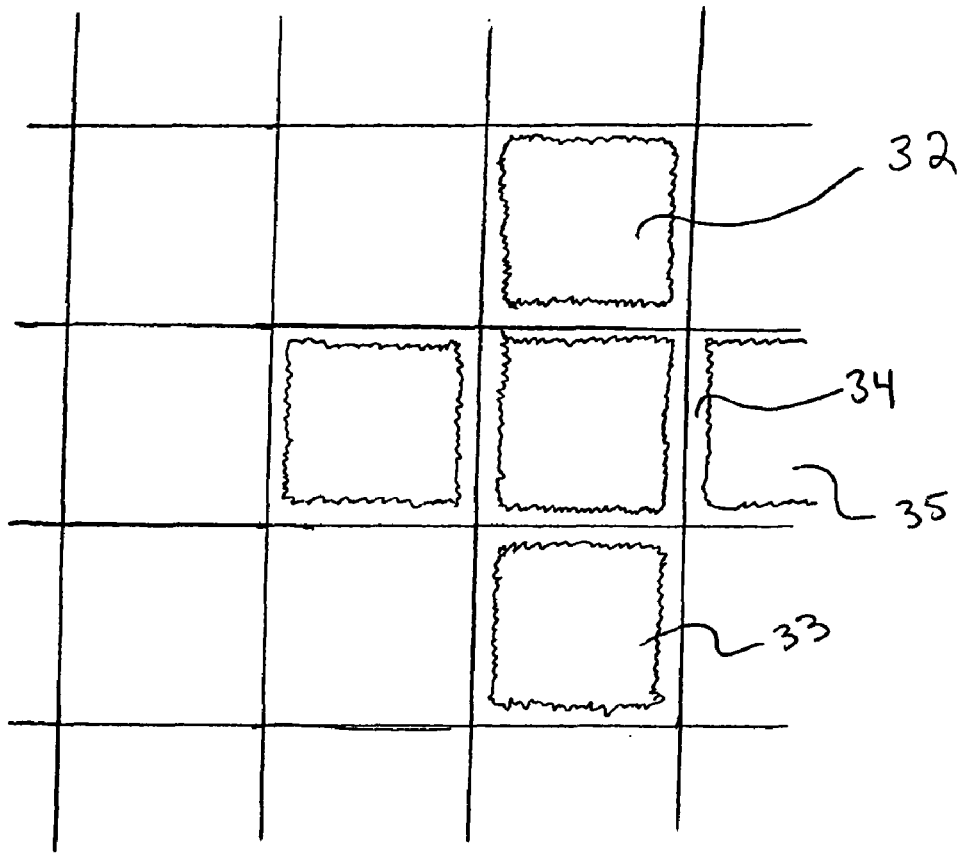
FIG. 2 is a close up view of the porous, flexible screen member from a skin removal apparatus.

FIG. 2 illustrates a close up view of the screen used in skin removal device 10. Screen member 30 consists of a plurality of holes 32, 33, 35 that penetrate the surface of screen member 30. In the illustrated embodiment, each hole, such as hole 32, is approximately 1/13"×1/13" is size. Hence, screen member 30 has approximately 144 holes per square inch, given the spacing between adjacent holes. The size and number of holes illustrated is not a requirement for the invention to operate as intended. The number of holes per square inch may vary significantly with the requirements of the design.

The abrasive material 34 covers the solid portion between adjacent holes of screen member 30. In the illustrated embodiment, abrasive material 34 is shown on a first surface of screen member 30. The abrasive material 34 may also cover the second surface of screen member 30 to form a skin removal device 10 with a double-sided exfoliating capability. In one embodiment, abrasive material 34 is silicon carbide, a material often used in drywall sandpaper. Silicon carbide is a man made material produced by combining silica sand and carbide at temperatures between 1600 and 2500 degrees Celsius. The resulting product has a number of extremely small crystals with razor sharp edges. Since the size of the crystals are small, they are not harmful to the skin. However, the number of crystals provide an abrasive surface capable of removing dead skin cells.

Different coarsenesses or grits of silicon carbide may be used for differing effects in removing dead skin cells. The larger the silicon carbide crystals, the smaller the grit number and the greater the coarseness of screen member 30. A plurality of different grits may be used for purposes of skin removal device 10. A smaller grit number removes more dead skin than a larger grit number; however, the resulting skin may be more coarse. A larger grit number removes less skin, but leaves a smoother finish.

Two methods are typically used to combine silica sand and carbide. The first is through the use of Acheson furnaces. However, the purity of the resulting product can vary according to the crystals distance to the graphite resistor that is used as the heat source. Clear, pale yellow and green crystals have the highest purity, and are found closest to the resistor. The color changes to blue and black at greater distances from the resistor. The darker crystals are less pure and usually doped with aluminum. The second method uses chemical vapor deposition, which uses a physical vapor transport commonly known as modified Lely method. Either method may be used for purposes of the present invention, but quality of the abrasive surface 34 may vary.

Silicon carbide is not required for use of abrasive surface 34. Other materials that provide similar strength and abrasive characteristics may be used without deviating from the scope and spirit of the invention.

Figure 3:
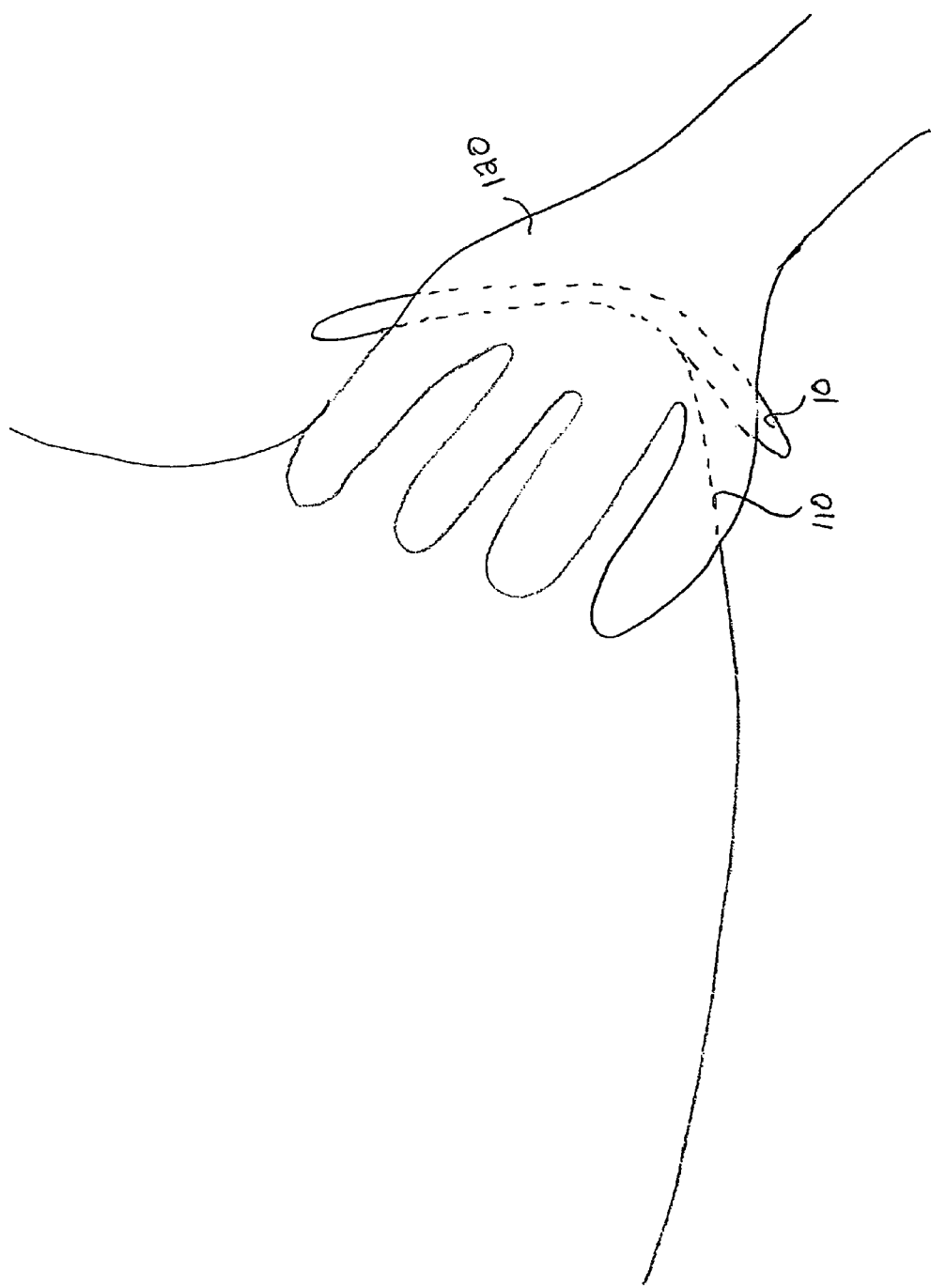
FIG. 3 is a depiction of using a skin removal apparatus to remove dry skin from a heel.

FIG. 3 illustrates utilizing a skin removal device 10 for sanding an area to be exfoliated, and more particularly, removing dead and dry skin from the surface of an individual's heel. Device 10 is placed in the palm 120 of a person's hand. As stated above, device 10 comprises a flexible sanding screen. Since the screen member 30 of skin removal device 10 is flexible, device 10 conforms to the shape of a person's heel, as illustrated in FIG. 3.

More particularly, in operation, skin removal device 10 is placed in the palm 120 of a user's hand. The user then presses the device 10 against the area to be exfoliated, such as heel 110 in the illustrated embodiment. A back-and-forth or circular motion applied to device 10 removes the dead skin. The amount of pressure may vary depending on how much skin is to be removed. The greater the pressure increases the amount of skin removed. The exfoliated skin passes through the screen member 30 and rests on top of the screen member, away from the surface of the screen member 30 that contacts the area to be exfoliated. In an alternate operation, the skin removal device 10 comprises a two-sided abrasive surface screen where both sides have an abrasive material disposed thereon. Either side may be pressed against the area to be exfoliated and used according to the method.

A user may also utilize a lower grit number (or high coarseness) to remove large amounts of skin, yet leaving a coarse finish. A user may then follow up with a higher grit number (less coarseness) to remove less skin but, leave a smoother finish on the exfoliated area, such as the heel. A user may then apply moisturizer after exfoliating to further soften the skin.

Typically, for the most effective use of skin removal device 10, the area to be exfoliated should be dry when removing dead or dry skin from the area. Accordingly, it is recommended a period of time passes after the area has been washed or moisturized before using skin removal device 10. A wet or moist area may result in the exfoliated skin cells clogging the holes in flexible screen member 30. A skin removal device 10 is typically used once and then discarded, as continued use of the device will reduce its effectiveness for exfoliating dead or dry skin cells.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as the invention.

I claim:

1. A method for exfoliating dead skin from an area of a human body, said method comprising:
   providing a skin removal device having a flexible screen member conformable to a first area of said human body to be exfoliated and a flexible first border member, said screen member having a first surface and a second surface, said first surface having an abrasive material disposed thereon, said first border member attached to an outside edge of said screen member wherein said flexible screen member has a plurality of different grits wherein each grit range is capable of removing varying amounts of dry skin;
   positioning said first surface of said screen member over said first area, said first surface contacting said first area;
   applying pressure to said second surface to create friction between said first surface of said screen member and said first area; and
   moving said screen member over said first area so that skin from said first area is removed and passes through screen member to said second surface.

2. The method of claim 1, further comprising:
   providing said flexible screen member having an abrasive material disposed on said second surface;
   positioning said second surface of said flexible screen member over a second area of said human body to be exfoliated, said second surface contacting said second area;
   applying pressure to said first surface to create friction between said second surface of said flexible screen member and said second area; and
   moving said screen member over said second area so that skin from said second area is removed and passes through said screen member to said first surface.

3. The method of claim 2, wherein said first area and said second area are the same.

4. A skin removal device comprising:
   a flexible screen member having a first surface and a second surface, said first surface having an abrasive material disposed thereon, said flexible screen member capable of conforming to an area to be exfoliated; and wherein said flexible screen member has a plurality of different grits wherein each grit range is capable of removing varying amounts of dry skin;
   a flexible first border member attached to said screen member, said first border member adapted for grasping by a hand and moving said flexible screen member over said area to be exfoliated.

5. The skin removal device of claim 4 further comprising a flexible second border member attached to said screen member, said second border member adapted for grasping by a hand and moving said flexible screen member over said area to be exfoliated.

6. The skin removal device of claim 4 wherein said first border member is disposed on all sides of said flexible screen member and completely surrounds the perimeter of said flexible screen member.

7. The skin removal device of claim 6 wherein said first border member is constructed of a single piece of material.

8. The skin removal device of claim 4 wherein the border member material is selected from a group consisting of foam, flexible plastic, polyurethane and rubber.

9. The skin removal device of claim 4, wherein said abrasive material is silicon carbide.

10. The skin removal device of claim 4, wherein said first border is affixed to at least a portion of said first surface and said second surface of said flexible screen member.

11. The skin removal device of claim 5, wherein said first border and second border are affixed to at least a portion of said first surface and said second surface of said flexible screen member.

12. The skin removal device of claim 4, wherein said second surface has an abrasive material disposed thereon.

13. The skin removal device of claim 4, wherein said flexible screen member has a plurality of holes disposed thereon.

* * * * *